United States Patent [19]

Ausec et al.

[11] Patent Number: 5,782,758

[45] Date of Patent: Jul. 21, 1998

[54] METHOD AND APPARATUS FOR IDENTIFYING THE PRESENCE OF NOISE IN A TIME DIVISION MULTIPLEXED OXIMETER

[75] Inventors: Larry B. Ausec, Boulder; Richard Frey, Louisville, both of Colo.

[73] Assignee: Ohmeda Inc., Liberty Corner, N.J.

[21] Appl. No.: 717,954

[22] Filed: Sep. 23, 1996

[51] Int. Cl.$^6$ .................................................. A61B 5/00
[52] U.S. Cl. .................................................. 600/336
[58] Field of Search ........................ 128/633, 664, 128/665; 356/41; 600/322, 323, 330, 336, 473, 476

[56] References Cited

U.S. PATENT DOCUMENTS

| | | | |
|---|---|---|---|
| 4,486,657 | 12/1984 | Bush | 250/227 |
| 4,645,883 | 2/1987 | Horna et al. | 379/406 |
| 4,781,195 | 11/1988 | Martin | 128/633 |
| 4,891,649 | 1/1990 | Labaar et al. | 342/203 |
| 5,150,336 | 9/1992 | Sullivan et al. | 367/103 |
| 5,190,038 | 3/1993 | Polson et al. | 128/633 |
| 5,503,148 | 4/1996 | Pologe et al. | 128/633 |

*Primary Examiner*—Jennifer Bahr
*Assistant Examiner*—Eric F. Winakur
*Attorney, Agent, or Firm*—Roger M. Rathbun; Salvatore P. Pace

[57] ABSTRACT

Noise content in the output signal of a system using time division multiplexing (TDM) is measured to determine whether the output signal represents a reliable measurement. A "dark" channel in a TDM input signal may be used to isolate noise which is present in the input signal from desired informational content in the signal. The noise is processed to determine if any component of the noise will be "imaged" into the passband of the system. Any such components are then processed in a manner approximating the system transfer function to produce a noise signal indicative of the noise content of the system output signal. In one embodiment of the invention, the noise signal is used to remove noise from the output signal of the system.

27 Claims, 6 Drawing Sheets

METHOD AND APPARATUS FOR IDENTIFYING THE PRESENCE OF NOISE IN A TIME DIVISION MULTIPLEXED OXIMETER

FIELD OF THE INVENTION

The invention relates in general to the detection of noise in systems using time division multiplexing and is particularly apt for use in the detection of noise in pulse oximetry systems using time division multiplexing.

BACKGROUND OF THE INVENTION

Time division multiplexing (TDM) is a function used in data transmission systems which allows multiple information signals to be transferred on a single communications medium at the same time by allocating a unique repetitive time slot on the medium to each of the signals. A small portion of each information signal can then be transmitted over the medium in each time slot corresponding to that signal to create a multiplexed signal on the medium. At the end of the medium, the multiplexed signal can be demultiplexed resulting in a plurality of separate information signals.

TDM can be implemented in both analog and digital systems. In a digital TDM system, each time slot includes information in digital form (i.e., represented using a plurality of discrete states). Similarly, in an analog TDM system, each time slot includes information in analog form (i.e., represented as values in a continuum of values). Hybrid systems also exist in which a time division multiplexed signal is converted from analog to digital form, or vice versa.

In general, systems which use analog TDM are more prone to noise corruption than systems which use digital TDM. That is, noise at the input of an analog TDM system can often be of sufficient energy to corrupt an output signal of the system to the point where it is unusable. Depending on the type and location of the particular system, noise can come from any of a large number of sources. A common and particularly troublesome form of noise is electromagnetic interference (EMI). EMI is comprised of stray electromagnetic signals which are produced through the operation of nearby electrical devices or appliances. For example, electric motors and digital computers are notorious sources of EMI. These stray signals may be picked up at the front end of an analog TDM system and processed in the system along with a desired input signal. If the EMI signals are large enough in magnitude relative to the desired input signal, serious corruption of the output signal of the system may result.

Such considerations are of particular concern in medical systems which utilize analog TDM, such as pulse oximetry systems. Medical systems are generally used to measure some characteristic of a patient to aid in diagnosing or monitoring the condition of the patient. For example, pulse oximetry systems are used to monitor the oxygen saturation of a patient's blood and the patient's heart rate. In this regard, it is important that such systems provide an accurate and reliable indication of the characteristic being measured. If there is a possibility that a medical system is producing an inaccurate reading, because of noise for example, it is important that some indication be given to an operator that the present reading is unreliable.

SUMMARY OF THE INVENTION

One objective of the present invention is to provide a method and apparatus for accurately determining whether an output signal of a system using time division multiplexing (TDM) has been corrupted by noise and indicating such to an operator of the system.

Another objective of the present invention is to provide a method and apparatus for detecting noise at the input of a system using TDM and determining whether the noise will corrupt an output signal of the system.

Yet another objective of the present invention is to provide a method and apparatus for removing noise components from a system output signal which has been corrupted by noise.

A further objective of the present invention is to achieve the above-described objectives in a pulse oximetry system for determining the oxygen saturation level in a test subject's arterial blood.

To achieve the above objectives, a system is provided which may use a "dark" channel in a TDM input signal to isolate noise which is present in the input signal from desired informational content in the signal. The system processes the detected noise to determine if any component of the noise will be "imaged" into the passband of the system. Any such components are then processed in a manner approximating the system transfer function to produce a signal indicative of the noise content of the system output signal. This signal can be used to estimate the reliability of the system output signal and/or it can be used to compensate for noise in the output signal. An indication of the reliability of the output signal is then displayed to a system operator.

DETAILED DESCRIPTION

The present invention relates to a method and apparatus for identifying noise in a time division multiplexed system. The method and apparatus is capable of determining whether an output signal of the system will be corrupted by the detected noise and indicating such to an operator. In addition, means may be provided for removing the noise from the output signal of the system when corruption occurs.

In one embodiment, the present invention is implemented in a pulse oximetry system. Pulse oximetry is a procedure for determining the level of oxygen saturation in a test subject's arterial blood based on the level of light absorption displayed by the subject's blood at multiple wavelengths (typically 660 nm and 940 nm). The procedure is quick, accurate, and non-invasive and therefore has become a preferred method in hospitals. Pulse oximetry systems generally use a TDM signal to carry blood absorption information from the test subject to processing circuitry where the information is analyzed and the saturation value is calculated. Before arriving at the processing circuitry, the TDM signal may be modulated by a noise signal, such as an EMI signal from a nearby medical instrument, which may corrupt the oxygen saturation measurement produced by the system.

Figure 1:
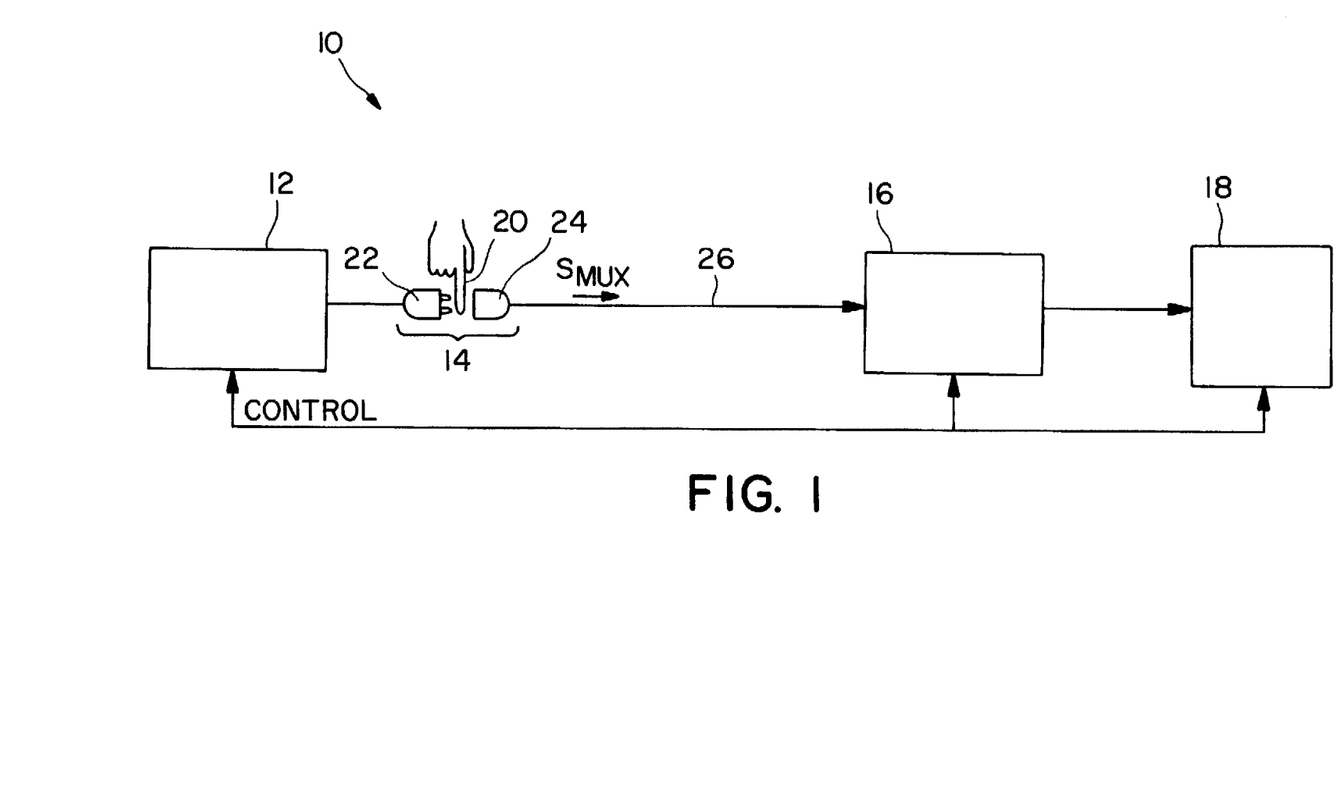
FIG. 1 is a block diagram illustrating a pulse oximetry system which may utilize the present invention.

FIG. 1 illustrates a pulse oximetry system which may utilize the method and apparatus of the present invention. For purposes of convenience, the pulse oximetry system will be referred to herein as system 10. As illustrated in FIG. 1, the system 10 includes: a control unit 12, a probe 14, a processing unit 16, and a display device 18. The probe 14 is operative for obtaining the light absorption information from the test subject. In this regard, the probe 14 is adapted to fit over a portion of the test subject's body which is rich in arterial blood flow, such as the test subject's finger 20. The probe 14 includes a first portion 22 which is capable of producing light at at least two different center wavelengths. The first portion 22 is placed against a first side of the test subject's finger 20 (or other suitable appendage) so that the light is directed into the finger 20. The probe 14 also includes a second portion 24 which includes light detection means, such as a photodiode, for detecting the intensity of the light after it has been transmitted through the finger 20. The intensity of the transmitted light is then used to calculate the level of oxygen saturation in the test subject's arterial blood.

To perform a saturation measurement, the system 10 operates as follows. The control unit 12 delivers a signal to the first portion 22 of the probe 14 instructing it to produce alternating pulses of light at the two (or more) center wavelengths. These alternating pulses of light are transmitted through the finger 20 of the test subject after which they are detected by the light detection means within the second portion 24 of the probe 14. The light detection means converts the transmitted light signal into a multiplexed electrical signal, Smux. The multiplexed signal is delivered, via transmission means 26, to the processing unit 16 where it is analyzed to determine the oxygen saturation level of the test subject's blood. After the saturation value is calculated, the value is delivered to the display device 18 for display to an operator.

Figure 2A:
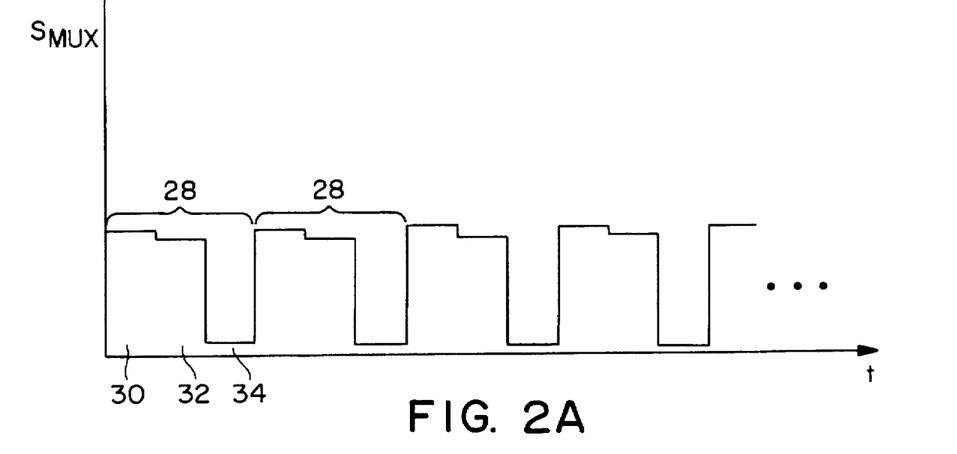
FIGS. 2A and 2B illustrate a typical pulse oximetry probe signal.
Figure 2B:
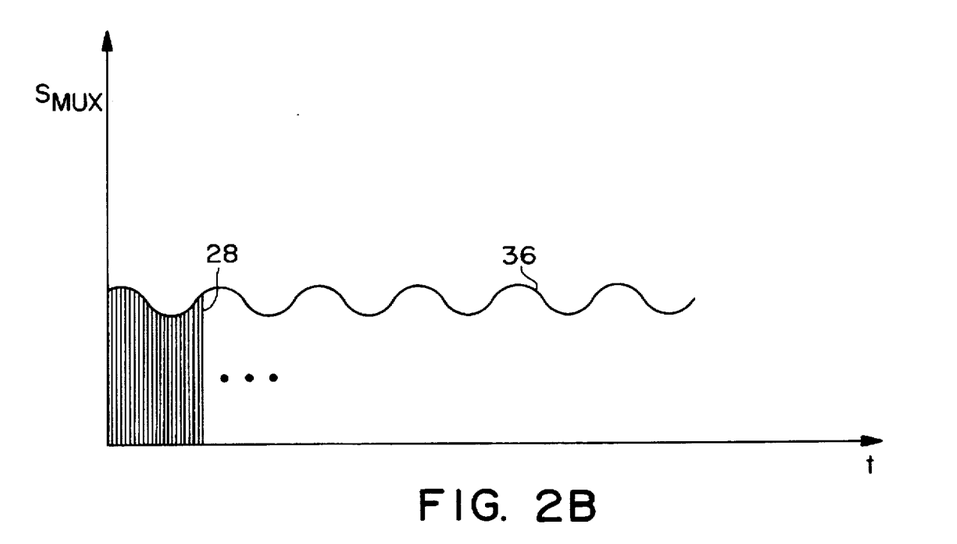

FIGS. 2A and 2B are graphs illustrating a typical pulse oximeter probe output signal, Smux. The two graphs each use a different time base to illustrate the overall makeup of the signal. FIG. 2A, for example, uses a reduced time base to illustrate the multiplexed nature of the signal, Smux. As seen in the figure, the signal is divided into a series of frames 28, wherein each frame 28 is divided into three distinct time slots 30, 32, 34. The first and second time slots 30, 32 in each frame 28 include light intensity information for the transmitted pulses of light at the first and second center wavelengths, respectively. The third time slot 34 includes, among other things, information indicating the intensity of ambient light which is impinging upon the second portion 24 of the probe 14. This ambient light may originate from a number of sources (such as the sun, room lights, operating theater lights, etc.) and its intensity is measured during a period (i.e., the third time slot, referred to herein as the darktime) when no light is being produced by the first portion 22 of the probe 14. The ambient light creates a DC offset over the entire multiplexed signal and, therefore, must be compensated for before an accurate saturation reading can be made.

FIG. 2B illustrates the signal, Smux, using an expanded time base. The figure shows a low frequency envelope waveform 36 which is formed by the frames 28 of the signal over an extended period of time. The envelope waveform 36 represents the pulsing of the test subject's arterial blood flow, i.e., the signal is at the frequency of the test subject's heart rate. It is this pulsatile (or AC) portion of the Smux signal that allows the processing unit 16 to calculate the oxygen saturation level of the test subject's arterial blood. This is because the pulsatile portion of the Smux signal relates solely to the light absorption of the arterial blood and ignores the light absorption of the venous blood, tissue, and pigmentation within the test subject's finger.

Figure 3:
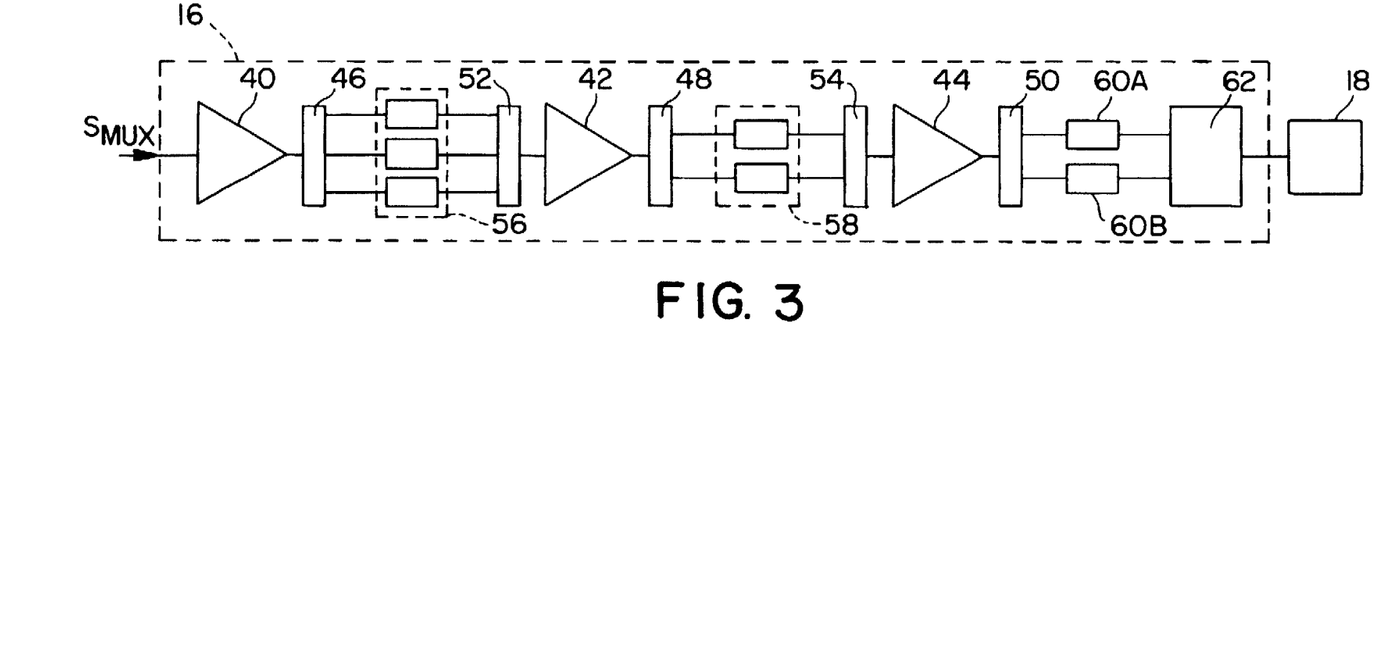
FIG. 3 a block diagram illustrating typical processing circuitry in a pulse oximetry system.

FIG. 3 is a block diagram illustrating a processing unit 16 which may be used in the system 10 of FIG. 1. The processing unit 16, as described above, is operative for receiving the signal, Smux, and processing the signal to determine the oxygen saturation level of the test subject's arterial blood. The processing unit 16 includes a plurality of amplification/filtration stages for conditioning the Smux signal, analog to digital (A/D) converter means for digitizing components of the signal, and digital signal processing unit for processing the digitized components to determine the saturation level. More specifically, the processor unit 16 comprises: a preamplifier means 40; a DC amplifier means 42; an AC amplifier means 44; a plurality of demultiplexing means 46, 48, 50; a plurality of multiplexing unit 52, 54; a first and second filter bank 56, 58; a pair of high order low pass filters 60A, 60B; and a digital signal processing means 62 with input A/D conversion.

The preamplifier means 40 receives the Smux signal from the probe 14 and amplifies the signal to a level which can be filtered. This amplification stage is important because the signal from the probe is generally very small. Demultiplexer 46 receives the amplified signal and separates it into three signals (a first corresponding to the first wavelength of light, a second corresponding to the second wavelength of light, and a third corresponding to the ambient light) for filtration purposes. Each of the three signals is filtered in a separate filtering means in filter bank 56 after which the signals are recombined into a single signal in multiplexer 52. Somewhere in this portion of the amplification/filtration chain, the ambient light data carried in the third time slot of the Smux signal is subtracted out from the Smux signal to compensate for the ambient light noise.

The recombined signal from multiplexer 52 is thereafter amplified in DC amplifier means 42 and is then again separated, filtered, and recombined using demultiplexer 48, filter bank 58, and multiplexer 54. However, this stage of processing only separates the Smux signal into two separate signals, one corresponding to each of the two center frequencies of light, because the ambient light information has already been subtracted out. The recombined signal from multiplexer 54 is then amplified in AC amplifier means 44 after which it is divided into two signals using demultiplexer 50. Each of the two signals are then filtered using low pass filters 60A, 60B and converted to digital form and processed in digital signal processing means 62. Digital signal processing means 62 then delivers a saturation value to display means 18 for display to an operator.

As discussed previously, problems arise when a noise signal modulates the Smux signal before the Smux signal reaches the processing means 16, i.e., before the Smux signal is amplified by the preamplifier means 40. This is because the Smux signal is very small in amplitude before it reaches the preamplifier 40 and, therefore, a relatively small noise signal can significantly reduce the signal to noise (S/N) ratio of the Smux signal. In addition, the transmission means 26 conveying the Smux signal to the processing unit 16 generally includes less RF shielding than the processing unit 16 which compounds the problem. The noise component of the Smux signal is carried through the processing means 16, resulting in an inaccurate saturation measurement at the output.

In past oximetry systems, decisions as to the quality of the saturation measurement were made, in part, by detecting the existence of RF energy in the input signal, Smux. If an undesirable RF component were present and had a magnitude greater than a given level, the saturation measurement was deemed corrupted. This method of determining the quality of a saturation measurement can result in the rejection of many reliable measurements because the existence of a spurious RF component in the input signal does not always corrupt the output signal.

In conceiving of the present invention, it was appreciated that not all out-of-band noise components in the Smux signal will corrupt the saturation measurement of the oximeter. For the most part, it is only the out-of-band components which will "image" into the passband of the processing means 16 that can destroy the accuracy of the oximeter reading. In one embodiment of the present invention, the passband of the processing means 16 extends from approximately 0.45 Hz to approximately 7.5 Hz. Therefore, the saturation reading will be corrupted by out-of-band noise only if a noise component is somehow transposed (i.e., imaged) into this relatively narrow range of frequencies and is of the requisite magnitude.

Figure 4:
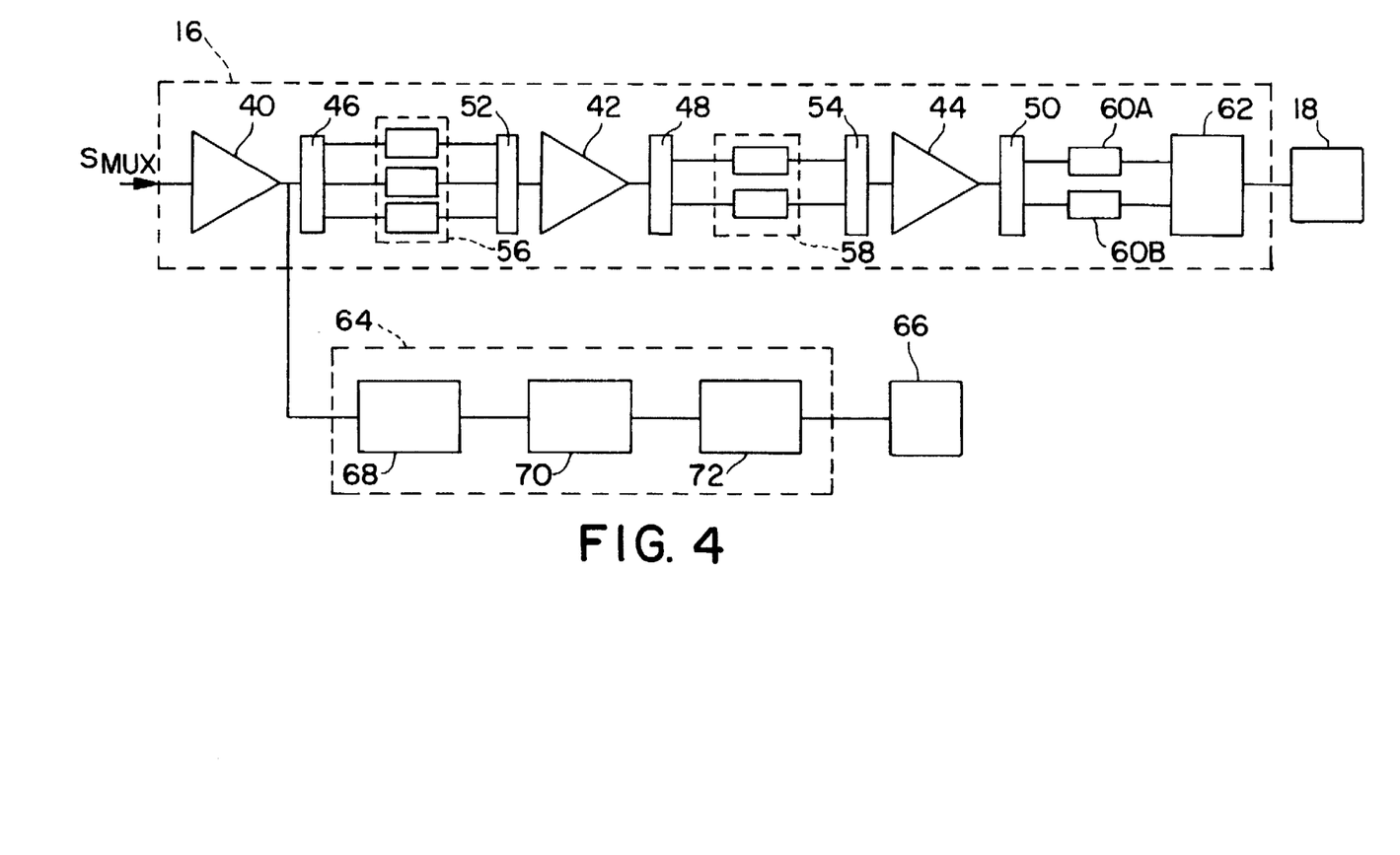
FIG. 4 is a block diagram illustrating circuitry in accordance with one embodiment of the present invention.

FIG. 4 illustrates a portion of a pulse oximetry system in accordance with the present invention. The system includes noise circuitry 64 for determining whether noise in the Smux signal will corrupt the saturation measurement of the oximeter. The noise circuitry 64 generally operates in parallel with the processing means 16 and is capable of generating an output signal on a display device 66 (which can be the same as display device 18) indicating the reliability of a current saturation reading. The noise circuitry 64 includes: imaging means 68, circuit emulation means 70, and comparison means 72. The imaging means 68 is operative for determining whether noise components in the Smux signal will be imaged into the passband of the processing means 16. The circuit emulation means 70 is operative for processing noise components identified by the imaging means 68 in a manner which approximates the transfer function of the processing means 16. The comparison means 72 compares a noise level determined by the circuit emulation means 70 to a predetermined threshold level to determine whether the current saturation reading of the oximeter is potentially corrupted.

The imaging means 68 receives the amplified Smux signal from the preamplifier 40 and processes the signal to identify noise components in the Smux signal which will be imaged into the passband of the processing means 16. In general, a noise component at one frequency in a signal can be imaged to another frequency any time the signal undergoes a nonlinear circuit response. For example, if a signal having noise components is sampled at a predetermined rate (using a switch, for example), the frequency of the noise components can be shifted in frequency due to aliasing. Similarly, if the signal is input into a circuit having a nonlinear gain, noise components can be shifted in frequency due to heterodyning effects. The imaging means 68, therefore, mimics nonlinear responses in the processing means 16 to create a noise signal which identifies noise components which will most likely be imaged into the passband of, and therefore processed by, the processing means 16.

The circuit emulation means 70 processes the noise signal produced by the imaging means 68 according to a transfer function that approximates the transfer function of the processing means 16 (without the preamplifier 40). Therefore, the output signal of the circuit emulation means 70 is indicative of noise levels in the digital signal processing means 62 which may interfere with the saturation calculation. If these noise levels are greater than a predetermined threshold level (found either empirically or through calculation), the accuracy of the saturation measurement of the oximeter will be compromised.

The comparison means 72 compares the output signal of the circuit emulation means 70 to the predetermined threshold level. If the peak of the output signal exceeds the threshold level, the comparison means 72 delivers a signal to the display device 66 indicating the same. The display device 66 then displays a message to an operator indicating that the current saturation reading is unreliable. If the peak does not exceed the threshold level, the operator is not notified and may assume the reading is accurate.

Figure 5:
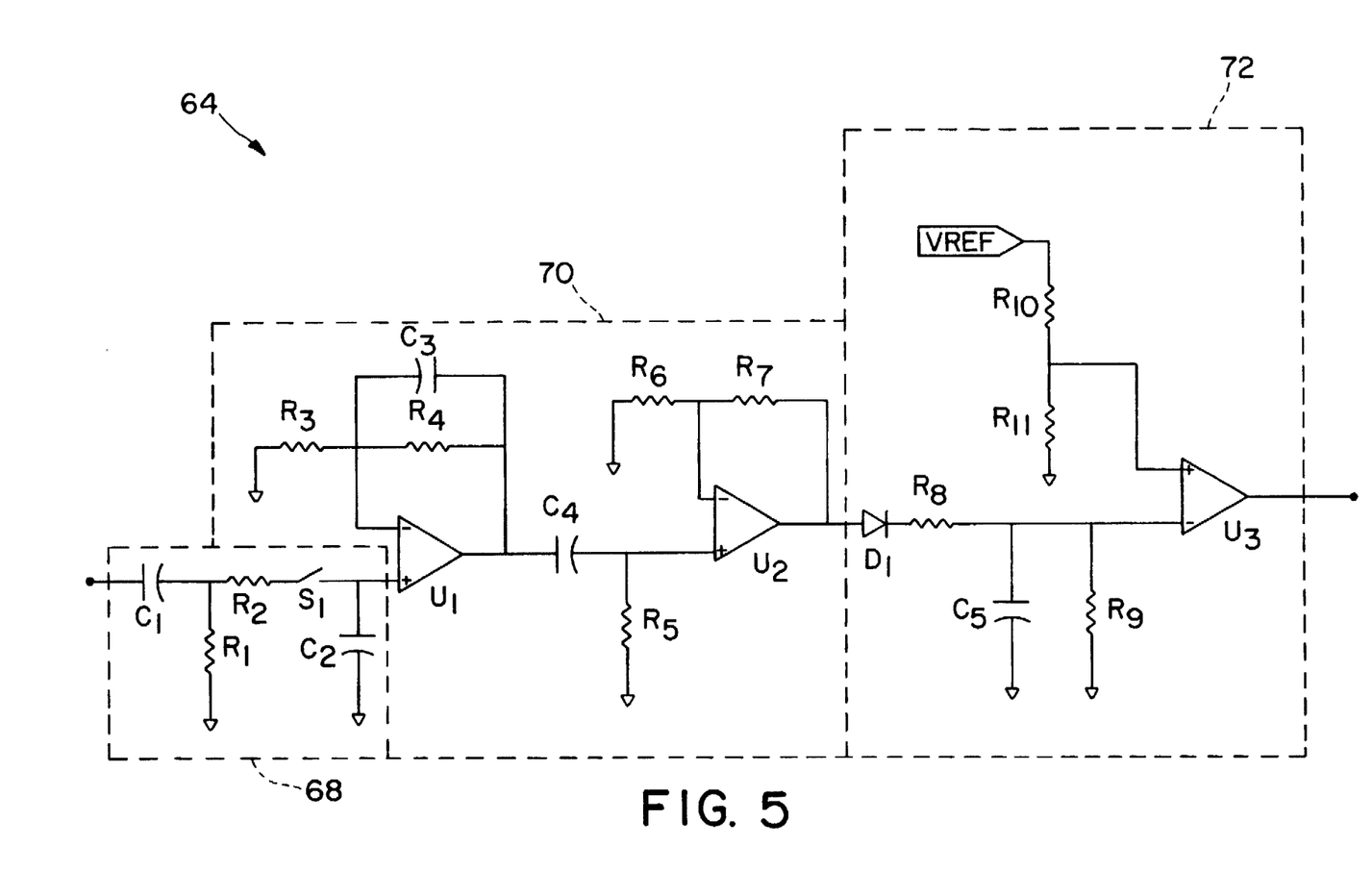
FIG. 5 is a schematic circuit diagram illustrating circuitry used in accordance with one embodiment of the present inventing.

FIG. 5 is a schematic diagram illustrating noise circuitry 64 in accordance with one embodiment of the present invention. As described above, the noise circuitry 64 comprises: imaging means 68, circuit emulation means 70, and comparison means 72. The imaging means 68 includes: capacitors C1 and C2; resistors R1 and R2; and a switching means S1. The combination of capacitor C1 and resistor R1 forms a high pass filter having a predetermined cutoff frequency. The cutoff frequency is chosen so that only potentially damaging noise components in the Smux signal may pass, i.e., switching noise (at 480 Hz) and other low frequency noise is blocked. In one embodiment of the present invention, the cutoff frequency is about 4800 Hz.

The combination of resistor R2 and capacitor C2 (assuming a given duty cycle of switch S1) forms a low pass filter having a cutoff frequency similar to the upper frequency in the passband of the processing means 16. This filter, therefore, approximates the passband of the processing means 16 (which in one embodiment is 0.45 Hz to 7.5 Hz). To ensure that noise components are not missed, the passband of the low pass filter can be made slightly larger than the passband of the processing means. In one embodiment of the present invention, the cutoff frequency of the low pass filter is 10 Hz.

The switching means S1 is responsible for creating the non-linear circuit response which images noise components in the Smux signal into the passband of the processing means 16. The switching means S1 is switched at the repetition rate of the Smux signal (i.e., 480 Hz in one embodiment of the present invention) so that it is closed during one portion (i.e., time slot) of the Smux signal and is open during the other portions of the signal. In this regard, the switching means S1 is similar to switches in the processing means 16 which are used to multiplex/demultiplex the Smux signal. The switching means S1 may include any type of analog switching device capable of switching at the desired rate. In one embodiment of the present invention, an integrated analog CMOS switch is used.

The switching means S1 images noise signals into the passband of the processing means through the aliasing characteristics of the discrete time system. In other words, by sampling the signal at the output of the high pass filter at a predetermined rate using the switching means S1, a beat frequency is created between noise components in the signal and the sampling rate. If this beat frequency is 10 Hz or below, the aliased signal components will appear across capacitor C2. If noise components appear across capacitor C2, then similar noise components will most likely be proceeding through the processing means 16.

The circuit emulation means 70 of FIG. 5 includes: operational amplifiers U1 and U2; resistors R3–R7; and capacitors C3 and C4. The components are configured to produce a transfer function which approximates a nominal transfer function of the hardware/software components of the processing means 16. The values of the circuit elements were empirically tuned until an effective model of the hardware/software transfer function was achieved. The first operational amplifier U1 in combination with resistors R3 and R4 and capacitor C3 produce a band limited gain with a cutoff frequency of 10 Hz. Capacitor C4 blocks the DC offset integrated on capacitor C2 and, in combination with resistor R5, provides high frequency pass characteristics similar to the hardware/software system. Operational amplifier U2 and resistors R6 and R7 provide an additional voltage gain which sets the gain of the whole circuit emulation means 70 to a typical operational gain of the processing means 16.

The comparison means 72 comprises: a diode D1; a capacitor C5; three resistors R9–R11; a comparator U3; and a reference voltage source Vref. Diode D1 and capacitor C5 form a peak detector for determining the peak voltage of the noise signal from the circuit emulation means 70. Resistors R8 and R9 moderate the response of the peak detector to a pulse train. The comparator U3 compares the level of the detected peak to a predetermined threshold level (produced by dividing Vref using R10 and R11) to create a digital signal indicative of whether the oximeter saturation measurement has been corrupted. The digital signal may then be delivered to a display device.

Figure 6:
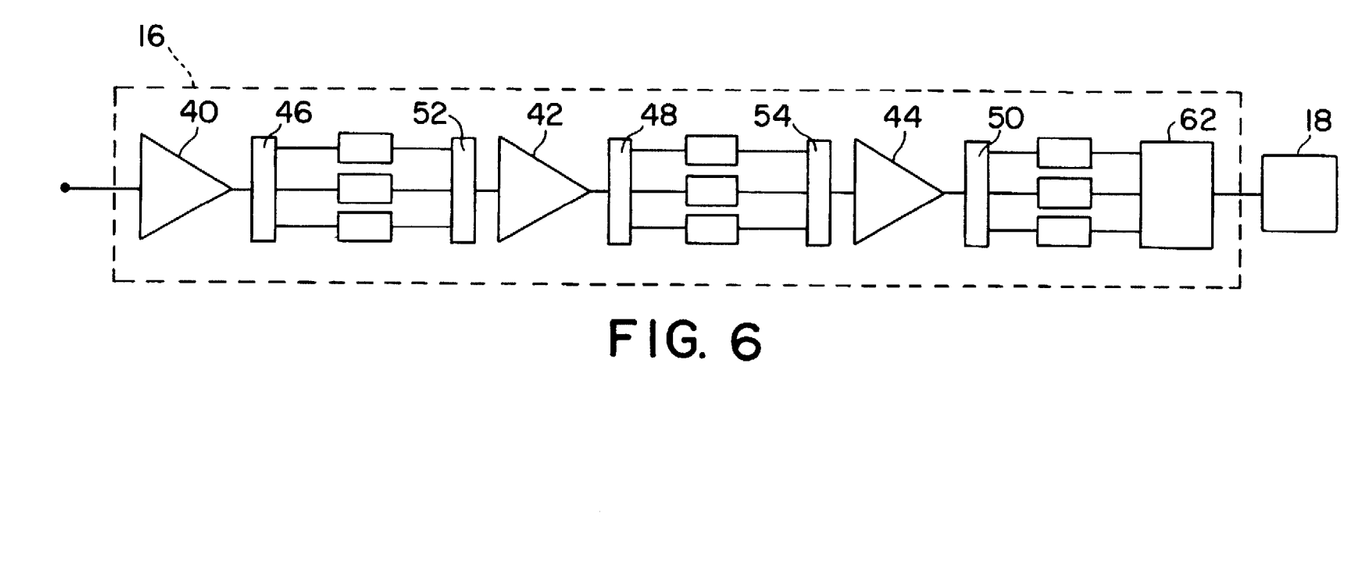
FIG. 6 is a block diagram illustrating circuitry in accordance with another embodiment of the present invention.

FIG. 6 illustrates another system in accordance with the present invention. In this embodiment, a third channel is provided through the entire length of the processing means 16. This third channel is operative for processing the darktime information in the Smux signal for use by the digital signal processing means 62 to determine the quality of the saturation measurement. Because the darktime information is processed substantially identically to the transmitted light information, any noise components which will image into the transmitted light channels will also image into the darktime channel. DC offset values caused by ambient light impinging upon the light detection means in the probe 14 are subtracted from the light intensity channels as before.

The noise signal resulting from the processing of the darktime information is a very accurate indicator of the noise content of the signals used to calculate the saturation value in the digital signal processing means. Accordingly, the noise signal can be used to calculate a S/N ratio for each of the signals for use in making a decision as to the quality of a saturation measurement. For example, it could be determined empirically that a S/N ratio of less than 5 to 1 produces an unreliable saturation reading. If such a ratio occurs, the digital signal processing means 62 can instruct the display device 18 to display a "unreliable reading" indication. Alternatively, the display device 18 can display a message such as "reposition probe" or "shield probe" so that a cleaner input signal can be achieved. In addition to the above, the system of FIG. 6 can also be used to detect spurious signals that are not the result of aliasing. For example, a low frequency signal at the output of the preamplifier means 40 may result from the detection of the modulation envelope of a stray RF signal. The system of FIG. 6 is capable of detecting such a signal.

It should be appreciated that the system of FIG. 6 may include any number of gain/filtration stages. For example, the signals out of multiplexer 46 can be immediately converted to digital form using a bank of A/D converters and additional gain and filtering operations can be performed in the digital signal processor 62. This approach would also permit the use of frequency domain processing and analysis to determine the quality of the saturation measurement. For example, the digital signal processing means 62 can include Fast Fourier Transform (FFT) circuitry for operating on the signal from the darktime channel. The output signal of the FFT will indicate the frequency components of the noise. These frequency components may be indicative of a particular type of interference, in which case a special message, which is specific to that type of interference, can displayed to the operator.

The digital signal processing means 62 can also perform an FFT operation on the light intensity signals from the other two channels. This would allow a frequency domain comparison to be done between the spectrum of the darktime signal and the spectrums of the light intensity signals. If the spectrums of the light intensity signals display a component which is the same as a component in the darktime signal, the digital signal processing means 62 can subtract that component from the intensity signals to remove the effect of the noise before calculating the saturation value.

In another embodiment, the multiplexed signal at the output of the preamplifier means 40 can be split so that the light intensity signals are processed in standard analog circuitry, such as processing means 16 in FIG. 4, while the darktime information is immediately converted to digital form in an A/D converter and processed digitally. This requires the digital simulation of the transfer function of the processing means 16.

Although the present invention has been described in conjunction with one of its embodiments, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. A pulse oximetry system using time division multiplexing, said system comprising:

means for transmitting light of a first wavelength through an appendage of a test subject to create a first transmitted light signal;

means for transmitting light of a second wavelength through said appendage to create a second transmitted light signal, wherein said second wavelength is different from said first wavelength;

means for creating a multiplexed signal using said first transmitted light signal and said second transmitted light signal;

first signal processing means for processing said multiplexed signal to determine an oxygen saturation value for said test subject's arterial blood, said first signal processing means having a predetermined passband;

means for displaying said oxygen saturation value to an operator;

means for determining whether an AC noise component in said multiplexed signal has corrupted said oxygen saturation value determined by said first signal processing means; and, means for notifying said operator when said oxygen saturation value is corrupted.

2. The system, as claimed in claim 1, wherein:

said means for determining includes means for determining whether an out-of-band noise component in said multiplexed signal will be imaged into said predetermined passband of said first signal processing means.

3. The system, as claimed in claim 1, wherein:

said means for determining includes means for imaging an out-of-band noise component in said multiplexed signal into said predetermined passband of said first signal processing means.

4. The system, as claimed in claim 3, wherein:

said means for imaging only images said out-of-band noise component into said predetermined passband when said first signal processing means will also image said out-of-band noise component into said predetermined passband.

5. The system, as claimed in claim 3, wherein:

said means for imaging includes non-linear circuit means.

6. The system, as claimed in claim 3, wherein:

said means for imaging includes switching means being switched at a predetermined rate.

7. The system, as claimed in claim 3, wherein:

said means for determining further includes second signal processing means for processing said noise component imaged into said predetermined passband according to a transfer function approximating a transfer function of said first signal processing means, wherein said second signal processing means only processes noise components.

8. The system, as claimed in claim 7, wherein:

said means for determining further includes means for comparing an output of said second signal processing means to a predetermined threshold signal.

9. The system, as claimed in claim 1, wherein:

said multiplexed signal includes a first portion having no transmitted light information; and said means for determining utilizes said first portion of said multiplexed signal to detect said noise signal.

10. The system, as claimed in claim 1, wherein:

said means for creating a multiplexed signal includes optical detection means.

11. The system, as claimed in claim 1, wherein:

said means for notifying includes at least one of the following: means for blocking display of said oxygen saturation value by said means for displaying and means for indicating that a presently displayed saturation value is corrupted.

12. A self-diagnostic pulse oximetry system, comprising:

means for receiving a time division multiplexed (TDM) input signal, said TDM input signal having a first portion carrying both information and noise and a second portion carrying only noise;

means for processing said first portion according to a first transfer function to create a first output signal indicative of the oxygen saturation of a test subject's arterial blood;

means for displaying said first output signal to a system operator;

means for processing said second portion according to a second transfer function which approximates said first transfer function to create a second output signal indicative of the noise content of said first output signal;

means for determining whether said first output signal has been corrupted by noise, based on said second output signal; and means for notifying said system operator when said first output signal has been corrupted by noise.

13. The system, as claimed in claim 12, wherein:

said second transfer function is substantially the same as said first transfer function.

14. The system, as claimed in claim 12, wherein:

said means for determining includes means for analyzing said second output signal in the frequency domain to determine a type of noise present in said first output signal.

15. The system, as claimed in claim 14, wherein:

said means for notifying includes means for displaying an error message to a system operator based on the type of noise present in said first output signal.

16. The system, as claimed in claim 14, wherein:

said means for analyzing includes means for performing a Fast Fourier Transform (FFT) on said second output signal.

17. The system, as claimed in claim 14, further comprising:

means for removing noise components from said first signal based on noise components identified in said second signal during said frequency domain analysis of said second signal.

18. The system, as claimed in claim 12, wherein:

said means for determining includes means for computing a signal to noise (S/N) ratio using said first output signal and said second output signal and means for comparing said S/N ratio to a predetermined value.

19. The system, as claimed in claim 12, wherein:

said first portion of said TDM signal includes information regarding light transmission through a test subject's arterial blood at two separate wavelengths of light.

20. In a time division multiplexed oximetry system for non-invasively determining a percentage of oxygen saturation in a test subject's blood, a method for determining whether an output signal has been corrupted by noise, said method comprising the steps of:

providing a system having a predetermined transfer function;

providing a multiplexed input signal to said system, said input signal having a plurality of separate time slots including a first time slot carrying a first signal having an information portion and a noise portion and a second time slot carrying a second signal having only a noise portion;

processing said first signal in said system according to said predetermined transfer function to produce a first output signal;

providing signal processing means for approximating said predetermined transfer function;

processing said second signal using said signal processing means to produce a second output signal;

determining whether said first output signal has been corrupted by noise based on said second output signal; and notifying a system operator when said first output signal has been corrupted by noise.

21. The method, as claimed in claim 20, wherein:

said step of providing a system includes providing a system having both hardware and software components, wherein said predetermined transfer function is determined based on both hardware and software.

22. The method, as claimed in claim 20, wherein:

said first time slot carries light transmission information corresponding to a first wavelength of light;

said second time slot carries no light transmission information; and said multiplexed input signal further includes a third time slot carrying light transmission information corresponding to a second wavelength of light.

23. The method, as claimed in claim 20, wherein said step of providing a multiplexed input signal includes the steps of:

providing means for generating light at a first center wavelength and a second center wavelength in response to a control signal;

providing means for detecting light at said two separate wavelengths;

positioning said means for generating on a first side of an appendage of a test subject;

positioning said means for detecting on an opposite side of said appendage of said test subject;

providing said control signal to said means for generating light to produce an optical signal having a first portion at said first center wavelength, a second portion at said second center wavelength, and a third portion where no light is generated by said means for generating, wherein a portion of said optical signal is transmitted through said appendage of said test subject; and receiving said transmitted portion of said optical signal in said means for detecting light to produce said multiplexed input signal.

24. The method, as claimed in claim 20, wherein:

said step of providing signal processing means includes providing means having a transfer function that is approximately equal to a nominal transfer function of said system.

25. The method, as claimed in claim 20, wherein:

said step of providing signal processing means includes providing means having a transfer function that is substantially the same as said predetermined transfer function.

26. The method, as claimed in claim 20, wherein:

said step of providing a system includes providing a system having a plurality of channels, each channel having substantially the same transfer function, wherein said signal processing means includes one of said channels.

27. The method, as claimed in claim 20, wherein:

said step of determining includes comparing said second output signal to a predetermined threshold level.

* * * * *